(12) United States Patent
Fukazawa et al.

(10) Patent No.: US 7,990,535 B2
(45) Date of Patent: Aug. 2, 2011

(54) SURFACE STATE DETECTING APPARATUS

(75) Inventors: Kazuhiko Fukazawa, Kamakura (JP); Takeo Oomori, Hachioji (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 12/659,304

(22) Filed: Mar. 3, 2010

(65) Prior Publication Data

US 2010/0182593 A1 Jul. 22, 2010

Related U.S. Application Data

(63) Continuation of application No. 12/289,077, filed on Oct. 20, 2008, now Pat. No. 7,697,139, which is a continuation of application No. PCT/JP2007/000496, filed on May 9, 2007.

(30) Foreign Application Priority Data

May 10, 2006 (JP) .................................. 2006-131120

(51) Int. Cl.
*G01J 4/00* (2006.01)
(52) U.S. Cl. ........................................................ 356/369
(58) Field of Classification Search .................. None
See application file for complete search history.

(56) References Cited

U.S. PATENT DOCUMENTS

| | | | |
|---|---|---|---|
| 5,835,220 A | 11/1998 | Kazama et al. | |
| 6,452,671 B1 | 9/2002 | Uda et al. | |
| 6,690,469 B1 | 2/2004 | Shibata et al. | |
| 2004/0063232 A1* | 4/2004 | Komatsu et al. | ................ 438/18 |
| 2005/0084782 A1* | 4/2005 | Sentoku | .......................... 430/30 |
| 2006/0192953 A1 | 8/2006 | Fukazawa et al. | |
| 2006/0232769 A1 | 10/2006 | Sugihara et al. | |

FOREIGN PATENT DOCUMENTS

| | | |
|---|---|---|
| JP | U-05-030761 | 4/1993 |
| JP | A-2001-141657 | 5/2001 |
| JP | A-2002-116011 | 4/2002 |
| JP | A-2006-105951 | 4/2006 |
| WO | WO 2005/040776 A1 | 5/2005 |

OTHER PUBLICATIONS

Aug. 7, 2007 International Search Report for PCT/JP2007/000496.

\* cited by examiner

*Primary Examiner* — Tu T Nguyen
(74) *Attorney, Agent, or Firm* — Oliff & Berridge, PLC

(57) ABSTRACT

A surface inspection apparatus includes units illuminating repetitive patterns formed on a surface of a suspected substance and measuring a variation in an intensity of regular reflection light caused by a change in shapes of the repetitive patterns, units illuminating the repetitive patterns with linearly polarized light, setting an angle formed between a repetitive direction of the repetitive patterns and a direction of a plane of vibration of the linearly polarized light at a tilt angle, and measuring a variation in a polarized state of the regular reflection light caused by the change in the shapes of the repetitive patterns, and a unit detecting a defect of the repetitive patterns based on the variation in the intensity and the variation in the polarized state of the regular reflection light.

15 Claims, 7 Drawing Sheets

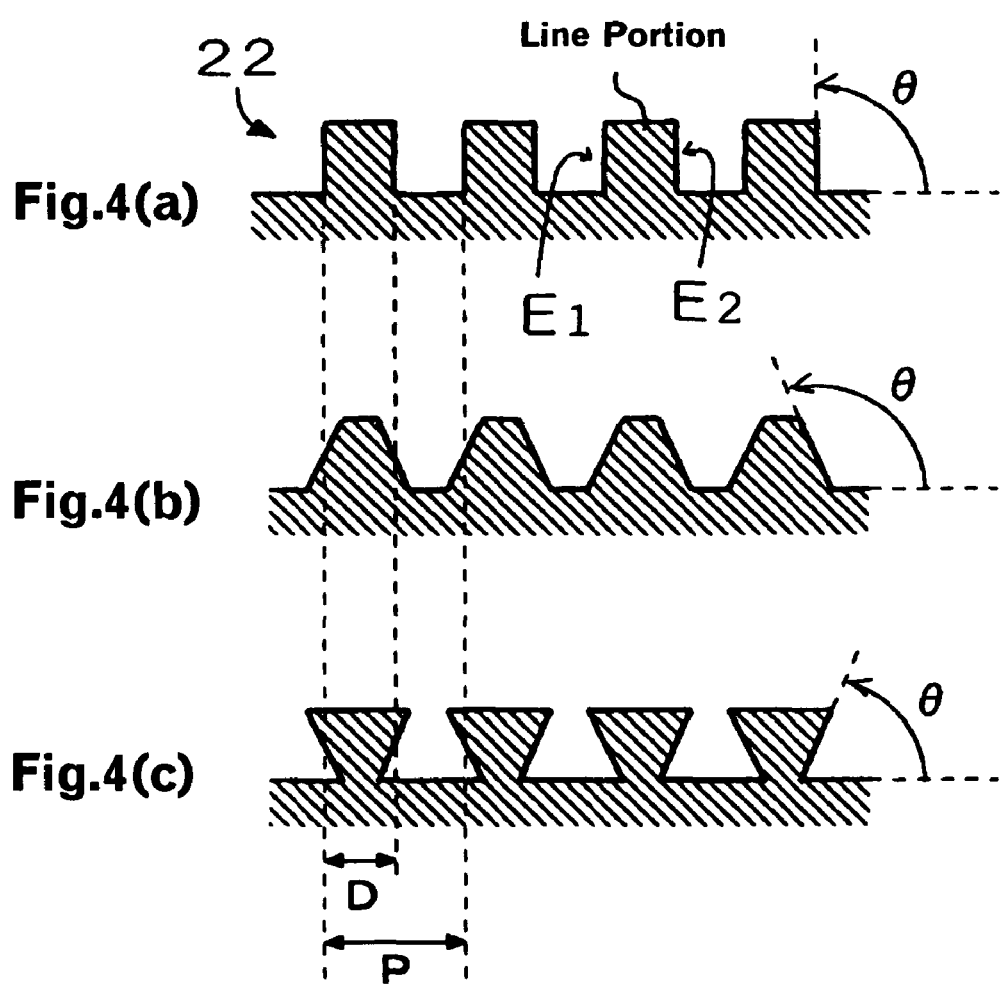

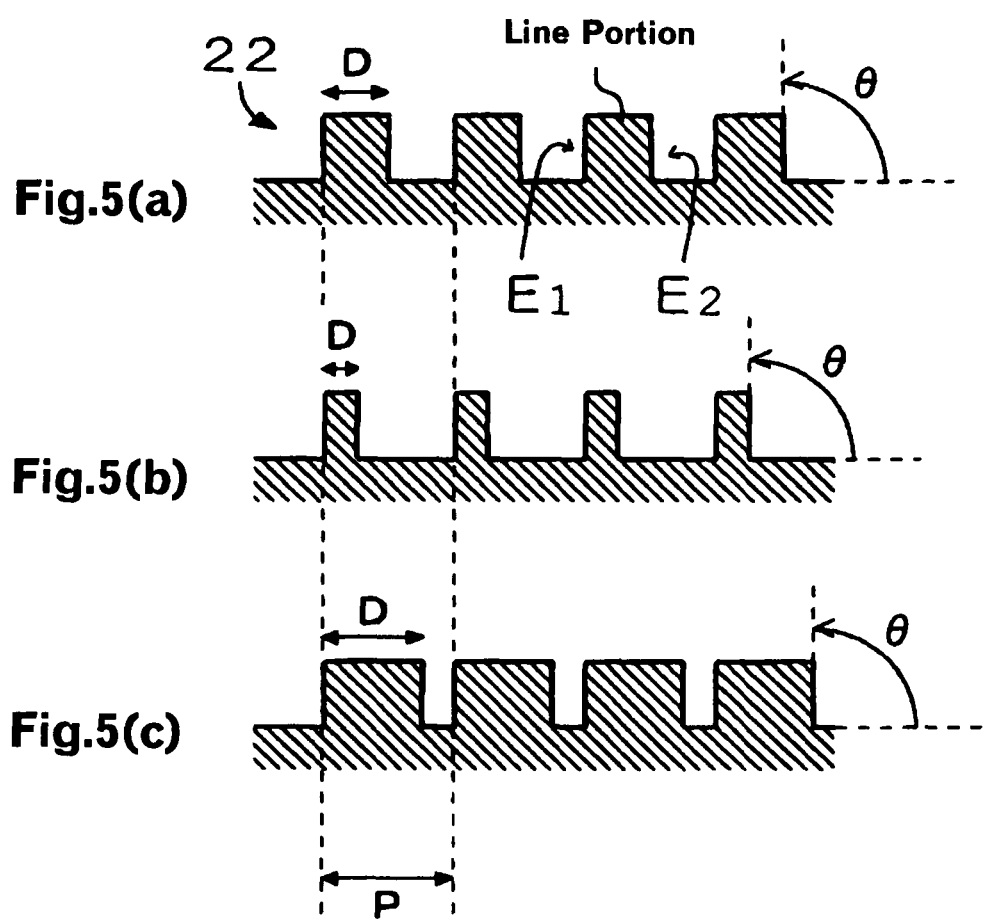

SURFACE STATE DETECTING APPARATUS

CROSS-REFERENCE TO RELATED APPLICATION

This application is a Continuation Application of U.S. patent application Ser. No. 12/289,077 filed Oct. 20, 2008, U.S. Pat. No. 7,697,139, and International Application No. PCT/JP2007/000496, filed May 9, 2007, designating the U.S., in which the International Application claims a priority date of May 10, 2006, based on prior filed Japanese Patent Application No. 2006-131120, the entire contents of which are incorporated herein by reference.

BACKGROUND

1. Field

The present application relates to a surface inspection apparatus executing a defect inspection of repetitive patterns formed on a surface of a suspected substance.

2. Description of the Related Art

There is known an apparatus which irradiates illumination light for inspection to repetitive patterns formed on a surface of a suspected substance (semiconductor wafer, liquid crystal substrate and the like, for instance), and executes a defect inspection of the repetitive patterns based on light generated from the repetitive patterns at this time. There are various methods applied to this inspection apparatus in accordance with a type of light (for instance, diffraction ray, scattered light, regular reflection light, and the like) generated from the repetitive patterns. Further, regarding the illumination light for inspection to be used, an apparatus using unpolarized light, an apparatus using linearly polarized light (refer to Patent Document 1: International Publication Pamphlet WO 2005/040776, for instance), and the like are known. Each of these inspection apparatus can collectively detect defects of the repetitive patterns in a relatively wide area (whole area, for instance) on the surface of the suspected substance, and can execute a defect inspection in a high throughput manner.

However, there are various types of defects of repetitive patterns. For example, as a typical type of defect generated at a time of an exposure on a suspected substance, a defocus defect and a dose defect can be cited. Under the present situation, it is difficult to separately detect the various types of defects in the aforementioned apparatus, so that a plurality of types of defects are collectively detected. However, as a result of repeated studies by the present inventors, it has been found that a detection sensitivity to the defect largely depends on a combination of the type and a detection method of the defect, and with a certain specific detection method, sufficient detection sensitivity cannot be obtained depending on the type of the defect. Further, it also has been found that even a defect in which sufficient detection sensitivity thereto cannot be obtained with a certain detection method can be detected in a highly sensitive manner by using another detection method.

SUMMARY

A proposition is to provide a surface inspection apparatus capable of securing sufficient detection sensitivity to a plurality of types of defects of repetitive patterns.

A surface inspection apparatus includes a first measuring unit, a second measuring unit, and a detecting unit. The first measuring unit illuminates repetitive patterns formed on a surface of a suspected substance and measures, based on a intensity of regular reflection light generated from the repetitive patterns, a variation in the intensity caused by a change in shapes of the repetitive patterns. The second measuring unit illuminates the repetitive patterns with linearly polarized light, sets an angle formed between a repetitive direction of the repetitive patterns and a direction of a plane of vibration of the linearly polarized light at the surface at a tilt angle, and measures, based on a polarized state of the regular reflection light generated from the repetitive patterns, a variation in the polarized state caused by the change in the shapes of the repetitive patterns. The detecting unit detects a defect of the repetitive patterns based on the variation in the intensity measured by the first measuring unit and the variation in the polarized state measured by the second measuring unit.

Another surface inspection apparatus includes an illuminating unit, a light receiving unit, a first processing unit, a second processing unit, and a detecting unit. The illuminating unit irradiates illumination light to repetitive patterns formed on a surface of a suspected substance and having a first polarization plate capable of being inserted into or removed from a light path of the illumination light. The light receiving unit outputs a light receiving signal based on regular reflection light generated from the repetitive patterns, and has a second polarization plate capable of being inserted into or removed from a light path of the regular reflection light and whose transmission axis intersects a transmission axis of the first polarization plate. The first processing unit disposes either of the first polarization plate or the second polarization plate in the light path, inputs the light receiving signal relating to a intensity of the regular reflection light from the light receiving unit, and measures a variation in the intensity caused by a change in shapes of the repetitive patterns. The second processing unit disposes both the first polarization plate and the second polarization plate in the light paths, sets an angle formed between a direction of a plane of vibration of linearly polarized light irradiated to the repetitive patterns as the illumination light at the surface and a repetitive direction of the repetitive patterns at a tilt angle, inputs the light receiving signal relating to a polarized state of the regular reflection light from the light receiving unit, and measures a variation in the polarized state caused by the change in the shapes of the repetitive patterns. The detecting unit detects a defect of the repetitive patterns based on the variation in the intensity measured by the first processing unit and the variation in the polarized state measured by the second processing unit.

Further, the first processing unit may dispose a polarization plate in the light path, the polarization plate being either of the first polarization plate or the second polarization plate whose transmission axis is orthogonal to a plane of incidence of the illumination light.

Further, the detecting unit may detect a first type of defect of the repetitive patterns based on the variation in the intensity, may detect a second type of defect of the repetitive patterns based on the variation in the polarized state, and may designate a spot on the surface where at least either of the first type of defect or the second type of defect is detected, as a final defect of the repetitive patterns.

Further, the detecting unit may output information on the final defect by adding information on a type of the defect thereto.

Further, the first type of defect may be a dose defect generated when performing an exposure on the suspected substance, and the second type of defect may be a defocus defect generated when performing an exposure on the suspected substance.

According to a surface inspection apparatus, it is possible to secure sufficient detection sensitivity to a plurality of types of defects of repetitive patterns.

BRIEF DESCRIPTION OF THE DRAWINGS

FIGS. 4(a), 4(b), and 4(c) are views to explain a defocus defect at a time of an exposure.

FIGS. 5(a), 5(b), and 5(c) are views to explain a dose defect at a time of an exposure.

DETAILED DESCRIPTION OF THE EMBODIMENTS

Hereinafter, embodiments will be specifically described with reference to the drawings.

Figure 1:
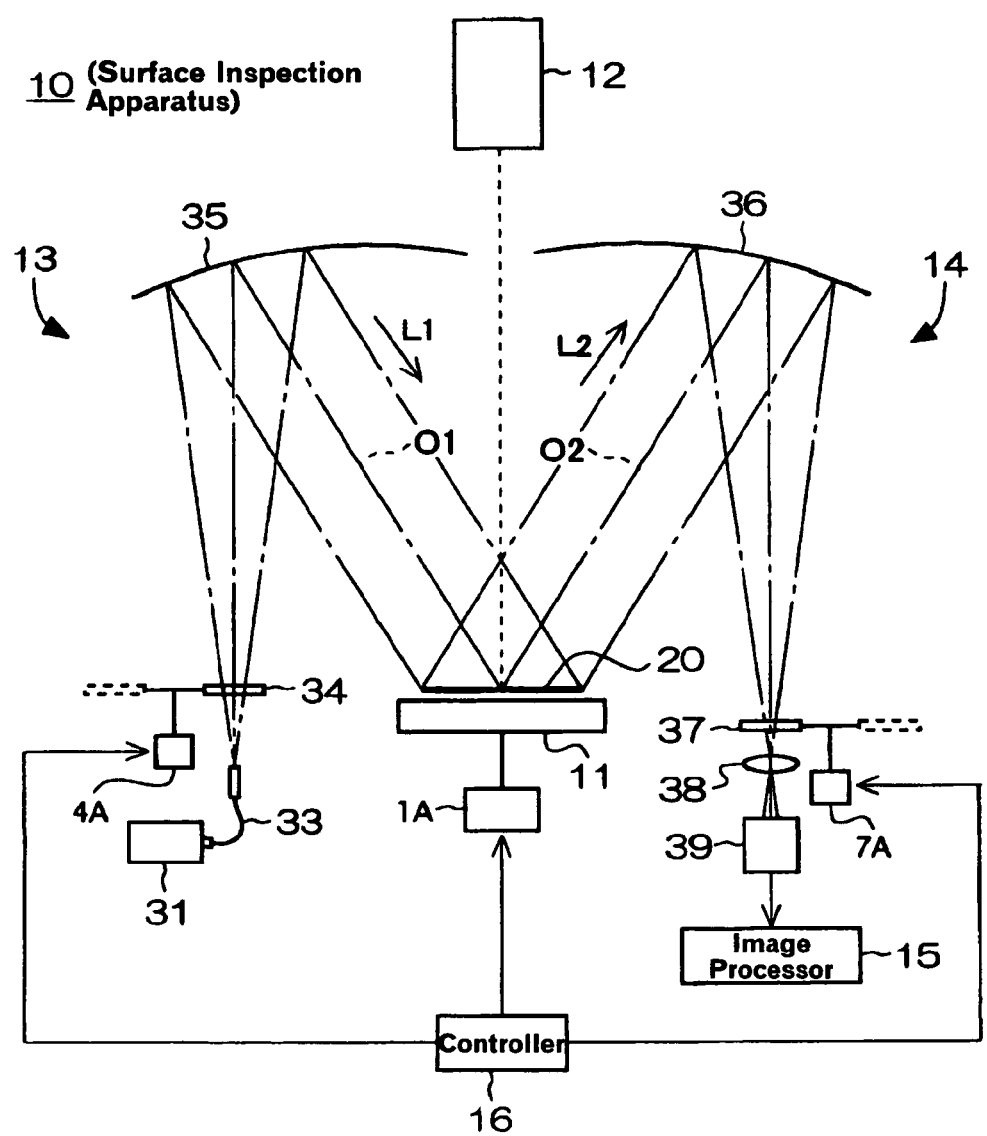
FIG. 1 is a view illustrating an entire structure of a surface inspection apparatus 10.

As illustrated in FIG. 1, a surface inspection apparatus 10 of this embodiment includes a stage 11 that supports a suspected substance 20, an alignment system 12, an illuminating system 13, a light receiving system 14, an image processor 15, and a controller 16.

Figure 2:
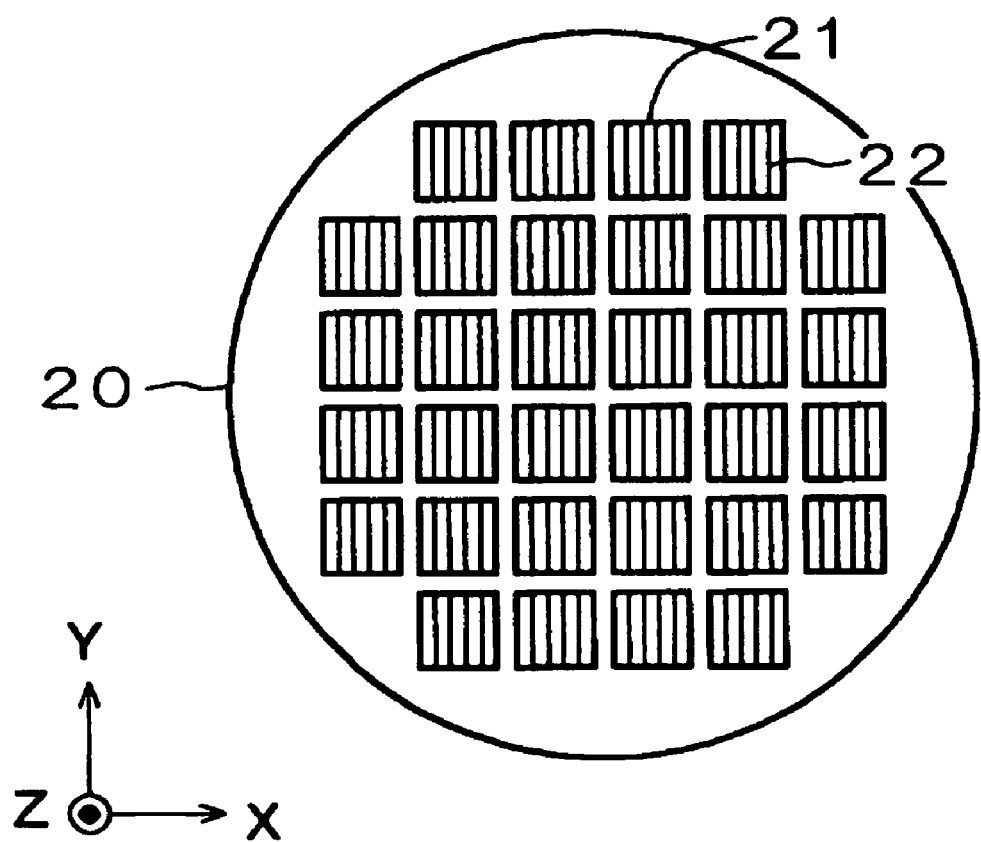
FIG. 2 is a schematic diagram of a surface of a suspected substance 20.

The suspected substance 20 is, for example, a semiconductor wafer, a liquid crystal glass substrate, or the like. As illustrated in FIG. 2, a plurality of chip areas 21 are arrayed on a surface (resist layer) of the suspected substance 20, and a repetitive pattern 22 to be inspected is formed in each of the chip areas 21. The repetitive pattern 22 is a pattern of line-and-space such as a wiring pattern. A direction along which line portions of the repetitive patterns 22 are arrayed (X direction) is referred to as a "repetitive direction of the repetitive patterns 22".

The surface inspection apparatus 10 of this embodiment is an apparatus which automatically executes a defect inspection of the repetitive patterns 22 formed on a surface of the suspected substance 20 during a process of manufacturing a semiconductor circuit element or a liquid crystal display element. In the surface inspection apparatus 10, the suspected substance 20 whose surface (resist layer) is exposed and developed is transferred from a cassette or a developing device by a not-illustrated transfer system and sucked to the stage 11.

The stage 11 holds fast the suspected substance 20 placed on an upper surface thereof by, for instance, vacuum suction. Besides, the stage 11 is provided with a rotary mechanism 1A. A rotary shaft of the stage 11 is orthogonal to the upper surface on which the suspected substance 20 is placed. The rotary mechanism 1A rotates the stage 11 in accordance with an instruction from the controller 16, to thereby rotate the suspected substance 20 placed on the upper surface of the stage 11. Accordingly, it is possible to rotate the repetitive direction (X direction in FIG. 2) of the repetitive patterns 22 of the suspected substance 20 within the surface of the suspected substance 20.

While the stage 11 rotates, the alignment system 12 illuminates an outer edge of the suspected substance 20, and detects a direction of the repetitive patterns 22 on the suspected substance 20 based on a position of an outer contour reference (a notch, for instance) along the rotating direction thereof provided at the outer edge. A detection result from the alignment system 12 is input into the controller 16, and when the repetitive direction (X direction) of the repetitive patterns 22 is set to be a desired direction, the rotation of the stage 11 is stopped.

For example, if a plane of incidence 3A of the illumination light L1 irradiated to the repetitive patterns 22 from the illuminating system 13 (FIG. 3) is set as a reference, the desired direction of the repetitive patterns is defined by an angle φ formed between a direction of the plane of incidence 3A and the repetitive direction (X direction) of the repetitive patterns 22. In this embodiment, the angle φ is set at a tilt angle) (0°<φ<90°). The angle φ is, for example, 45°. Note that the plane of incidence 3A is a plane including an irradiation direction of the illumination light L1 and a normal on the surface of the suspected substance 20.

The illuminating system 13 is a unit irradiating the illumination light L1 for inspection to the repetitive patterns 22 formed on the surface of the suspected substance 20 (FIG. 2 and FIG. 3) and includes a lamphouse 31, a light guide fiber 33, a polarization plate 34, and a concave reflecting mirror 35. The illuminating system 13 is a telecentric optical system with respect to a side of the suspected substance 20.

Although the illustration is omitted, inside the lamphouse 31, a light source, a wavelength selection filter, an ND filter used in a light quantity adjustment, and the like are embedded. The light source is an inexpensive discharge light source such as a halogen lamp, a metal halide lamp, and a mercury lamp. The wavelength selection filter selectively transmits a bright-line spectrum of a predetermined wavelength among light radiated from the light source.

The light guide fiber 33 transmits the light radiated from the lamphouse 31 and emits a divergent light flux of illumination light (unpolarized light).

Figure 3:
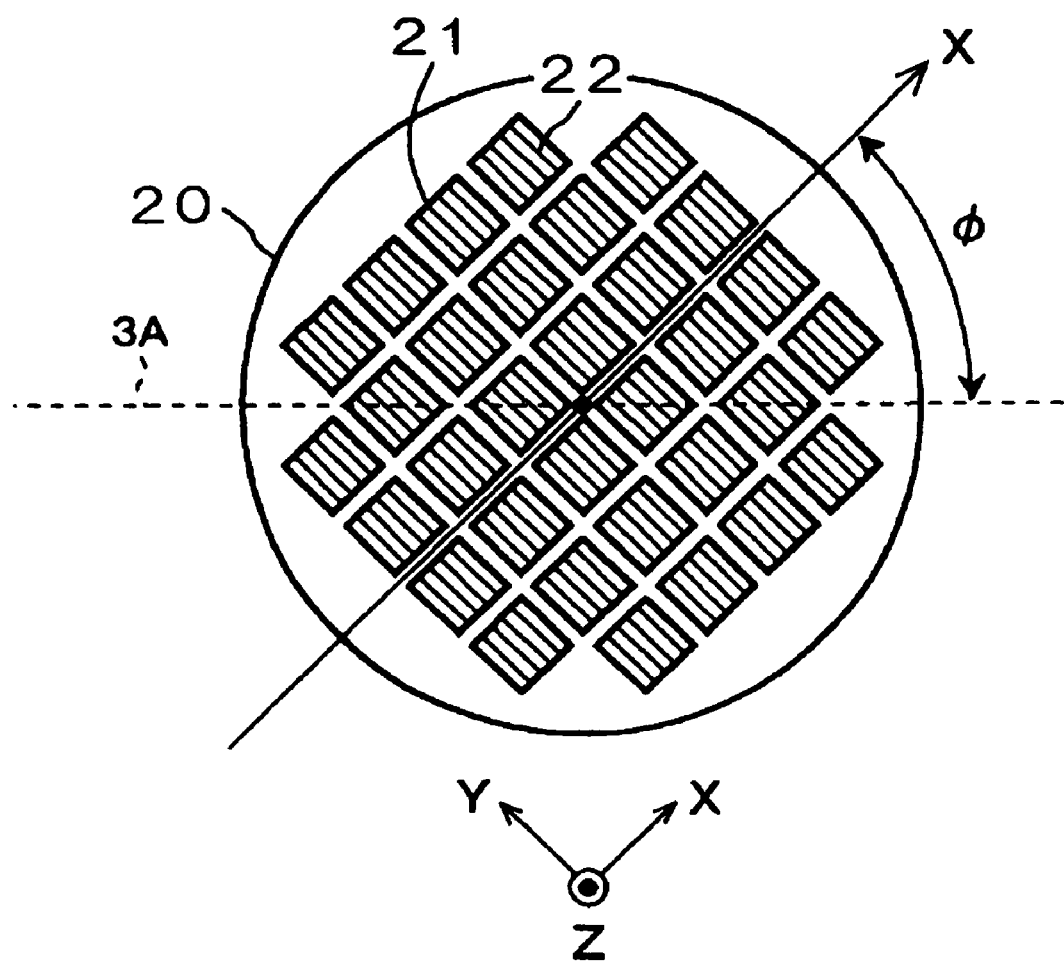
FIG. 3 is a view to explain an inclination state between a plane of incidence (3A) of illumination light L1 and a repetitive direction (X direction) of repetitive patterns 22.

The polarization plate 34 is disposed in the vicinity of an emission end of the light guide fiber 33, and its transmission axis is set at a predetermined direction. Subsequently, the polarization plate 34 converts the divergent light flux of illumination light (unpolarized light) emitted from the light guide fiber 33 to light in a polarized state (namely, linearly polarized light) according to the direction of the transmission axis. The direction of the transmission axis of the polarization plate 34 is parallel with the plane of incidence 3A of the illumination light L1 with respect to the repetitive patterns 22 (FIG. 3).

The concave reflecting mirror 35 is a reflecting mirror in which an inner side of a spherical surface is a reflection surface, and is disposed so that its front-side focal point substantially matches the emission end of the light guide fiber 33 and its rear-side focal point substantially matches the surface of the suspected substance 20. Accordingly, the divergent light flux of illumination light (linearly polarized light) from the polarization plate 34 is collimated at the concave reflecting mirror 35, and irradiated to the repetitive patterns 22 on the suspected substance 20 as the illumination light L1 for inspection.

Further, the aforementioned polarization plate 34 is structured so that it can be inserted into or removed from a light path between the light guide fiber 33 and the concave reflecting mirror 35 (namely, light path of the divergent flux of illumination light), and can retract from a position in the light path shown by a solid line to a position shown by a dotted line in FIG. 1. In order to realize this, a rotary shaft of a drive motor 4A is coupled to the polarization plate 34. The polarization plate 34 can rotate around the rotary shaft of the drive motor 4A as a center. The rotation (insertion and removal) of the polarization plate 34 is conducted by the drive motor 4A in accordance with the instruction from the controller 16.

When the polarization plate 34 is retracted from the light path, the divergent flux of illumination light (unpolarized light) from the light guide fiber 33 is directly incident to the concave reflecting mirror 35. Subsequently, the light is collimated at the concave reflecting mirror 35 and irradiated to the repetitive patterns 22 on the suspected substance 20 as the illumination light L1 for inspection.

As described above, in the aforementioned illuminating system 13, the repetitive patterns 22 can be illuminated by the linearly polarized illumination light L1 when the polarization plate 34 is disposed in the light path between the light guide fiber 33 and the concave reflecting mirror 35, and it can be illuminated by the unpolarized illumination light L1t when the polarization plate 34 is retracted from the light path.

Further, in any cases, the illumination light L1 is incident to respective points of a relatively wide area (whole area, for instance) of the surface of the suspected substance 20 from a diagonal upper direction in a substantially constant angle condition. This can be realized by diverging the light flux from the lamphouse 31 and then collimating it at the concave reflecting mirror 35. If the whole surface of the suspected substance 20 is illuminated, it becomes possible to collectively detect the defects of the repetitive patterns 22 in the whole surface and to execute the defect inspection in a high-throughput manner.

When the repetitive patterns 22 are illuminated by using the aforementioned linearly polarized or unpolarized illumination light L1, regular reflection light L2 is generated from the repetitive patterns 22. Note that in this embodiment, there is no chance that the repetitive pattern 22 generates diffraction ray when the illumination light L1 is irradiated thereto, since a pitch of the repetitive pattern 22 is sufficiently small compared to a wavelength of the illumination light L1.

The surface inspection apparatus 10 of this embodiment illuminates the repetitive patterns 22 on the surface of the suspected substance 20 with the linearly polarized or unpolarized illumination light L1, guides the regular reflection light L2 generated from the repetitive patterns 22 at this time to the light receiving system 14, and executes the defect inspection of the repetitive patterns 22 based on the intensity or the polarized state of the regular reflection light L2.

The light receiving system 14 is a unit outputting a light receiving signal based on the regular reflection light L2 generated from the repetitive patterns 22, and includes a concave reflecting mirror 36, a polarization plate 37, a condenser lens 38, and an image sensor 39. The light receiving system 14 is a telecentric optical system with respect to the side of the suspected substance 20.

The concave reflecting mirror 36 having the same structure as that of the concave reflecting mirror 35 of the illuminating system 13 reflects the regular reflection light L2 generated from the repetitive patterns 22 on the surface of the suspected substance 20 to convert it to a condensed light flux, and then guides it toward the polarization plate 37. Subsequently, the light (regular reflection light L2) from the concave reflecting mirror 36 transmits the polarization plate 37, and then is incident to the image sensor 39 via the condenser lens 38.

Note that the polarization plate 37 is structured so that it can be inserted into or removed from a light path between the concave reflecting mirror 36 and the condenser lens 38 (namely, light path of the condensed light flux of regular reflection light L2), and can retract from a position in the light path shown by a solid line to a position shown by a dotted line in FIG. 1. In order to realize this, a rotary shaft of a drive motor 7A is coupled to the polarization plate 37. The polarization plate 37 can rotate around the rotary shaft of the drive motor 7A as a center. The rotation (insertion and removal) of the polarization plate 37 is conducted by the drive motor 7A in accordance with the instruction from the controller 16.

When the polarization plate 37 is retracted from the light path, the regular reflection light L2 from the repetitive patterns 22 is directly (without passing through the polarization plate 37) incident to the image sensor 39. Further, when the polarization plate 37 is disposed in the light path, the regular reflection light L2 from the repetitive patterns 22 is incident to the image sensor 39 via the polarization plate 37.

When the polarization plate 37 is disposed in the light path, the disposed position thereof is in the vicinity of the condenser lens 38, and its transmission axis is set in a predetermined direction as follows. Specifically, the direction of the transmission axis of the polarization plate 37 is set to be orthogonal to the plane of incidence 3A of the illumination light L1 (FIG. 3).

Subsequently, regardless of the insertion/removal state of the polarization plate 37, a reflected image of the surface of the suspected substance 20 is formed at an imaging area of the image sensor 39 in accordance with the regular reflection light L2 from the respective points (repetitive patterns 22) on the surface of the suspected substance 20.

The image sensor 39 is disposed at a position conjugate with the position of the surface of the suspected substance 20. The image sensor 39 is, for example, a CCD image sensor or the like, which performs photoelectric conversion on the reflected image of the suspected substance 20 formed at the imaging area and outputs image signals (information regarding the regular reflection light L2) to the image processor 15.

Based on the image signals output from the image sensor 39, the image processor 15 takes the reflected image of the suspected substance 20. Subsequently, it performs a process to detect a defect of the repetitive patterns 22.

Next, a procedure of the defect inspection of the repetitive patterns 22 in the surface inspection apparatus 10 of this embodiment will be explained. Here, an explanation will be made regarding a detection of defects at a time of an exposure on the suspected substance 20 among defects of the repetitive patterns 22 (namely, defocus defect and dose defect). Incidentally, the defect at the time of the exposure appears in each shot area of the suspected substance 20.

The defocus defect is a defect generated when the amount of defocus at the time of the exposure on the suspected substance 20 (shift amount of a focus position when performing the exposure using an exposure apparatus) exceeds a tolerance level, and is appeared as a change in a shape of the repetitive pattern 22 (namely, change in inclined angles θ of edges $E_1$ and $E_2$ of the line portion), as illustrated in FIGS. 4(a), 4(b), and 4(c). When the focus at the time of the exposure takes a proper value (FIG. 4(a)), the edges $E_1$ and $E_2$ of the repetitive pattern 22 take vertical forms. When the focus value at the time of the exposure deviates from the proper value (FIGS. 4(b) and 4(c)), the edges $E_1$ and $E_2$ are inclined (θ≠90°. However, a pitch P of the repetitive pattern 22 and a line width D of the line portion are never changed depending on the defocus amount.

The dose defect is a defect generated when the amount of dose at the time of the exposure on the suspected substance 20 (exposure amount when performing the exposure using the exposure apparatus) exceeds or falls below a tolerance level, and is appeared as a change in a shape of the repetitive pattern 22 (namely, change in the line width D of the line portion), as illustrated in FIGS. 5(a), 5(b), and 5(c). When the dose amount at the time of the exposure takes a proper value (FIG. 5(a)), the line width D of the repetitive pattern 22 takes a design value. When the dose amount at the time of the exposure deviates from the proper value (FIGS. 5(b) and 5(c)), the line width D takes a value different from the design value. However, the pitch P of the repetitive pattern 22 and the inclined angles θ of the edges $E_1$ and $E_2$ of the line portion are never changed depending on the dose amount.

As a result of repeated studies by the present inventors regarding a detection of such two types of defects (defocus defect and dose defect), it has been found that by using two detection methods as follows, it is possible to separately detect the defocus defect and the dose defect.

With the use of a first detection method, sufficient detection sensitivity to the defocus defect can be secured, but, it is not possible to obtain sufficient detection sensitivity to the dose defect. Accordingly, if the first detection method is employed, the defocus defect of the repetitive patterns 22 can be selectively detected.

On the contrary, with the use of a second detection method, sufficient detection sensitivity to the dose defect can be secured, but, it is not possible to obtain sufficient detection sensitivity to the defocus defect. Accordingly, if the second detection method is employed, the dose defect of the repetitive patterns 22 can be selectively detected.

The surface inspection apparatus 10 of this embodiment can realize both the first detection method and the second detection method by structuring such that the polarization plate 34 of the illuminating system 13 can be inserted into or removed from the light path, and the polarization plate 37 of the light receiving system 14 can be inserted into or removed from the light path.

When executing the defect inspection of the repetitive patterns 22, the controller 16 gives instructions to control the drive motor 4A of the illuminating system 13 and the drive motor 7A of the light receiving system 14 so that the rotations (insertion and removal) of the two polarization plates 34 and 37 are conducted in a conjunction manner. Specifically, when either of the polarization plates 34 or 37 is disposed in the light path, the other one is also disposed in the light path, and when either of the polarization plates is retracted, the other one is also retracted from the light path. Subsequently, under respective situations where both the polarization plates 34 and 37 are disposed or retracted, processes as follows are conducted.

First, in order to selectively detect the defocus defect of the repetitive patterns 22 using the first detection method, both the polarization plates 34 and 37 are disposed in the light paths. At this time, the direction of the transmission axis of the polarization plate 34 of the illuminating system 13 is parallel with the plane of incidence 3A of the illumination light L1 (FIG. 3), as described above. Further, the direction of the transmission axis of the polarization plate 37 of the light receiving system 14 is orthogonal to the plane of incidence 3A of the illumination light L1. Specifically, the two polarization plates 34 and 37 are disposed so that their transmission axes are orthogonal to each other (disposition in a cross-Nicole state).

Subsequently, the repetitive patterns 22 are illuminated by the linearly polarized illumination light L1 obtained via the polarization plate 34 of the illuminating system 13, and the regular reflection light L2 generated from the repetitive patterns 22 at this time is incident to the image sensor 39 via the polarization plate 37 of the light receiving system 14.

Figure 6A:
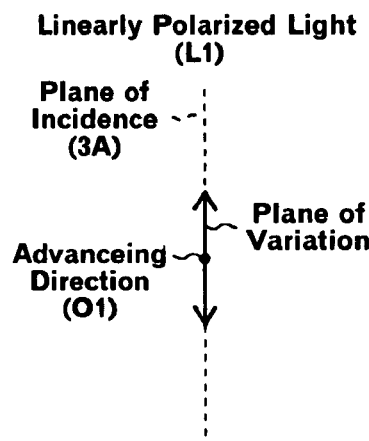
FIGS. 6(a), 6(b), and 6(c) are views to explain polarized states of the illumination light L1 and regular reflection light L2.

Here, in this embodiment, the linearly polarized illumination light L1 is p-polarized light. In other words, as illustrated in FIG. 6(a), a plane (plane of vibration of the illumination light L1) including an advancing direction of the illumination light L1 and a vibration direction of an electric (or magnetic) vector is included in the plane of incidence (3A) of the illumination light L1.

Figure 7:
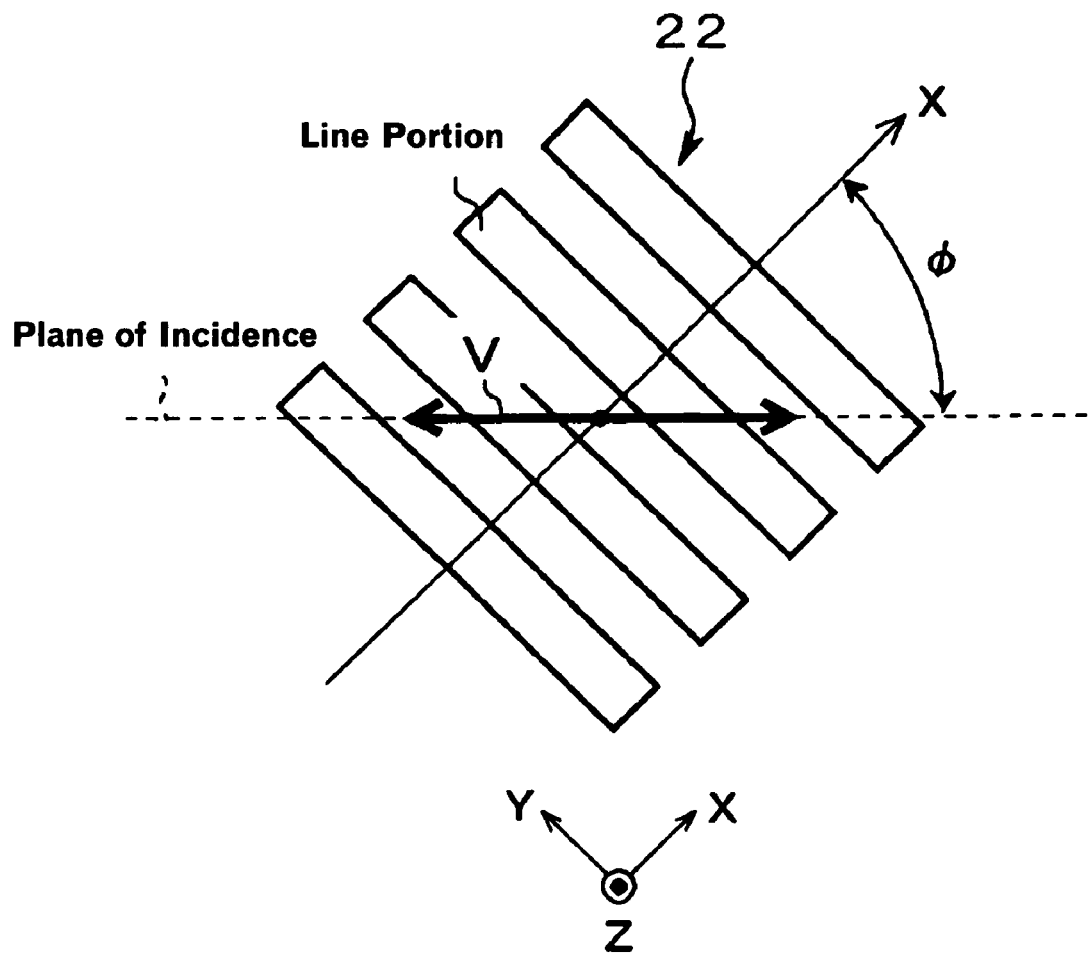
FIG. 7 is a view to explain an inclination state between a direction of a plane of vibration (V direction) of the illumination light L1 and the repetitive direction (X direction) of the repetitive patterns 22.

Therefore, when setting the angle θ formed between the direction of the plane of incidence 3A of the illumination light L1 (FIG. 3) and the repetitive direction (X direction) of the repetitive patterns 22 at a tilt angle (0°<φ<90°), the angle φ formed between the direction of the plane of vibration of the illumination light L1 (V direction) at the surface of the suspected substance 20 and the repetitive direction (X direction) of the repetitive patterns 22 can also be set at a tilt angle (0°<φ<90°), as illustrated in FIG. 7. The angle φ is, for example, 45°.

In other words, the linearly polarized illumination light L1 is incident to the repetitive patterns 22 in a state where the direction of the plane of vibration (V direction in FIG. 7) at the surface of the suspected substance 20 is inclined by the angle φ (45°, for instance) with respect to the repetitive direction (X direction) of the repetitive patterns 22, namely, in a state where it diagonally crosses the repetitive patterns 22.

Such a state of angle formed with the illumination light L1 and the repetitive patterns 22 is constant over the entire surface of the suspected substance 20. Note that even when an angle of 45° is instead expressed as an angle of 135°, 225° or 315°, the state of angle between the illumination light L1 and the repetitive patterns 22 is the same.

Subsequently, when the repetitive patterns 22 are illuminated by using the aforementioned illumination light L1 (linearly polarized light), an ovalization of the linearly polarized light (illumination light L1) is generated due to a form birefringence caused by an anisotropy of the repetitive patterns 22, resulting that elliptically polarized regular reflection light L2 (FIG. 6(b)) is generated from the repetitive patterns 22.

Figure 6B:
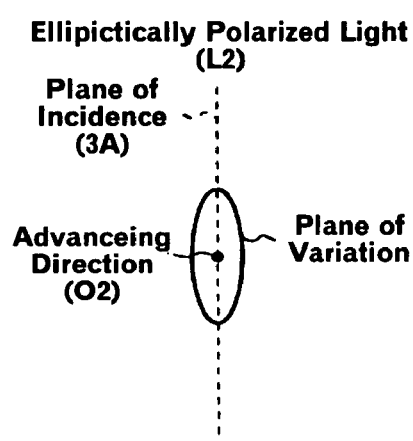
Figure 6C:
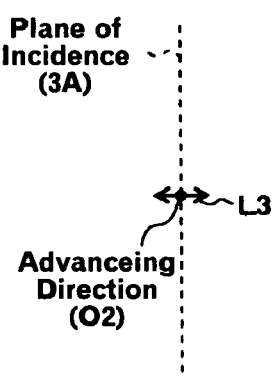

The ovalization of the linearly polarized light generated by the repetitive patterns 22 means that there is generated a new polarization component L3 (FIG. 6(c)) being orthogonal to a plane of vibration (here, which matches the plane of incidence of the illumination light L1) of the linearly polarized light incident to the repetitive patterns 22.

Further, the extent of the ovalization of the linearly polarized light can be represented by a size of the new polarization component L3 (FIG. 6(c)), and it largely changes depending on the change in the inclined angles θ of the edges $E_1$ and $E_2$ of the line portion of the repetitive pattern 22 (defocus defect) illustrated in FIGS. 4(a), 4(b), and 4(c), which was found out by the studies of the present inventors. Further, it was also found out that there is very little dependency on the change in the line width D of the line portion (dose defect) illustrated in FIGS. 5(a), 5(b), and 5(c).

Namely, it was found that in the respective points (repetitive patterns 22) on the surface of the suspected substance 20, even when the shape of the repetitive pattern 22 changes due to the change in the defocus amount or the dose amount when performing the exposure on the suspected substance 20 (FIGS. 4(a), 4(b), and 4(c) and FIGS. 5(a), 5(b), and 5(c)), the extent of the ovalization of the linearly polarized light (size of the polarization component L3 in FIG. 6(c)) is changed only by the change in the inclined angles θ of the edges $E_1$ and $E_2$ (defocus defect) illustrated in FIGS. 4(a), 4(b), and 4(c).

Further, it was also found that, as a tendency, the extent of the ovalization of the linearly polarized light (size of the polarization component L3 in FIG. 6(c)) becomes largest when the edges $E_1$ and $E_2$ of the line portion take vertical forms as illustrated in FIG. 4(a) (when focus at the time of the exposure takes a proper value), and it becomes smaller as the inclined angles θ of the edges $E_1$ and $E_2$ deviate from 90° as illustrated in FIGS. 4(b) and 4(c) (focus value at the time of the exposure deviates from the proper value).

As a result of such an ovalization of the linearly polarized light, the elliptically polarized regular reflection light L2 (FIG. 6(b)) is generated from the repetitive patterns 22. Note that since the specific description regarding the ovalization has been made in International Publication Pamphlet WO 2005/040776 already applied by the present applicant, a detailed explanation thereof will be omitted here. Further, as described above, since the pitch of the repetitive pattern 22 is sufficiently small compared to the wavelength of the illumination light L1, there is no chance that the diffraction ray is generated from the repetitive patterns 22.

The elliptically polarized regular reflection light L2 (FIG. 6(b)) generated from the repetitive patterns 22 when the linearly polarized illumination light L1 is irradiated thereto includes the aforementioned new polarization component L3 (FIG. 6(c)) generated by the ovalization of the linearly polarized light, and the size of the polarization component L3 represents a polarized state of the regular reflection light L2. Note that, as will be seen from the description above, the polarized state of the regular reflection light L2 (size of the polarization component L3 in FIG. 6(c)) largely changes depending on the change in the inclined angles θ of the edges $E_1$ and $E_2$ of the repetitive pattern 22 (defocus defect) illustrated in FIGS. 4(a), 4(b), and 4(c).

Therefore, in the first detection method, the regular reflection light L2 generated from the repetitive patterns 22 is guided to the light receiving system 14 (FIG. 1), and when the light transmits the polarization plate 37 in the light path of the light receiving system 14, the polarization component L3 of the regular reflection light L2 (FIG. 6(c)) is extracted. Subsequently, only the polarization component L3 is made to be incident to the image sensor 39, and based on the output from the image sensor 39, the reflected image of the suspected substance 20 is taken into the image processor 15.

On the reflected image of the suspected substance 20, there appears brightness/darkness corresponding to the size of the polarization component L3 of the regular reflection light L2 (FIG. 6(c)) generated from the respective points (repetitive patterns 22) on the surface of the suspected substance 20, namely, brightness/darkness corresponding to the polarized state of the regular reflection light L2. Note that the brightness/darkness of the reflected image changes in each shot area on the surface of the suspected substance 20, and is substantially in proportion to the size of the polarization component L3.

Further, as will be seen from the description above, the brightness/darkness of the reflected image of the suspected substance 20 largely changes depending on the change in the inclined angles θ of the edges $E_1$ and $E_2$ of the repetitive pattern 22 (defocus defect) illustrated in FIGS. 4(a), 4(b), and 4(c). As a tendency, the reflected image becomes brighter as the edges $E_1$ and $E_2$ take ideal forms being closer to vertical forms (FIG. 4(a)), and it becomes darker as the edges $E_1$ and $E_2$ deviate from the vertical forms (refer to FIGS. 4(b) and 4(c)).

Therefore, after taking the reflected image of the suspected substance 20, the image processor 15 compares brightness information on the reflected image with brightness information on a reflected image of a desirable sample. The desirable sample is a sample in which a focus at a time of an exposure is maintained at a proper value and repetitive patterns 22 with ideal forms (FIG. 4(a)) are formed on its whole surface. Further, the brightness information on the reflected image of the desirable sample is assumed to indicate the highest brightness value.

By setting the brightness value off the reflected image of the desirable sample as a reference, the image processor 15 measures a variation amount (namely, decrease amount) of the brightness value of the reflected image of the suspected substance 20. The obtained variation amount (decrease amount) of the brightness value represents a variation in the polarized state of the regular reflection light L2 caused by the change in the inclined angles θ of the edges $E_1$ and $E_2$ of the repetitive pattern 22 (FIGS. 4(a), 4(b), and 4(c)).

Subsequently, the image processor 15 detects the defocus defect of the repetitive patterns 22 based on the variation amount of the brightness value in the reflected image of the suspected substance 20 (namely, variation in the polarized state of the regular reflection light L2). For instance, if the variation amount of the brightness value is greater than a predetermined threshold value (tolerance value), it may be judged that there is a "defect", on the other hand, if the variation amount is less than the threshold value, the repetitive patterns may be judged to be "normal". Further, it is possible to compare the variation amount of the brightness value in the reflected image of the suspected substance 20 with a predetermined threshold value, instead of using the desirable sample.

As described above, in the first detection method, the repetitive patterns 22 are illuminated by the linearly polarized illumination light L1, the reflected image of the suspected substance 20 is taken in accordance with the polarized state of the regular reflection light L2 (size of the polarization component L3 in FIG. 6(c)) generated from the repetitive patterns 22, and based on the brightness/darkness of the reflected image, the variation in the polarized state of the regular reflection light L2 caused by the change in the inclined angles θ of the edges $E_1$ and $E_2$ of the repetitive pattern 22 (FIGS. 4(a), 4(b), and 4(c)) is measured.

Therefore, according to the first detection method, although the sufficient detection sensitivity to the dose defect (FIGS. 5(a), 5(b), and 5(c)) cannot be obtained, it is possible to secure the sufficient detection sensitivity to the defocus defect (FIGS. 4(a), 4(b), and 4(c)) of the repetitive patterns 22, so that the defocus defect can be selectively detected. Note that if the angle φ formed between the direction of the plane of vibration (V direction) and the repetitive direction (X direction) in FIG. 7 is set at 45°, it is possible to provide the highest detection sensitivity to the defocus defect of the repetitive patterns 22.

Next, in order to selectively detect the dose defect of the repetitive patterns 22 (FIGS. 5(a), 5(b), and 5(c)) using the second detection method, both the polarization plates 34 and 37 are retracted from the light paths. At this time, the repetitive patterns 22 are illuminated by the unpolarized illumination light L1, and the unpolarized regular reflection light L2 generated from the repetitive patterns 22 is directly (without passing through the polarization plate 37) incident to the image sensor 39. Subsequently, based on the output from the image sensor 39, the reflected image of the suspected substance 20 is taken into the image processor 15.

Note that even when the unpolarized illumination light L1 is used, the angle φ formed between the direction of its plane of incidence 3A (FIG. 3) and the repetitive direction (X direction) of the repetitive patterns 22 may be set at a tilt angle (0°<φ<90°), similarly as in the first detection method. Namely, when shifting the detection method from the first detection method to the second detection method, there is no need to change the direction of the repetitive patterns 22. In the second detection method, it is possible to make noise light (diffraction ray and the like, for instance) generated from the repetitive patterns 22 not to be guided to the light receiving system 14 by setting the angle φ at a tilt angle. Note that in the second detection method, the angle φ may be set at 0°.

On the reflected image of the suspected substance 20 taken into the image processor 15, there is appeared brightness/darkness corresponding to the intensity of the regular reflection light L2 (unpolarized light) generated from the respective points (repetitive patterns 22) on the surface of the suspected substance 20. Note that the brightness/darkness of the reflected image changes in each shot area on the surface of the suspected substance 20, and is substantially in proportion to the intensity of the regular reflection light L2.

Further, the brightness/darkness of the reflected image of the suspected substance 20 (∝ intensity of the regular reflection light L2) largely changes depending on the change in the line width D of the line portion of the repetitive pattern 22 (dose defect) illustrated in FIGS. 5(a), 5(b), and 5(c), which was found out by the studies of the present inventors. Further, it was also found out that there is very little dependency on the change in the inclined angles θ of the edges $E_1$ and $E_2$ of the line portion (defocus defect) illustrated in FIGS. 4(a), 4(b), and 4(c).

Namely, it was found that in the respective points (repetitive patterns 22) on the surface of the suspected substance 20, even when the shape of the repetitive pattern 22 changes due to the change in the defocus amount or the dose amount when performing the exposure on the suspected substance 20 (FIGS. 4(a), 4(b), and 4(c) and FIGS. 5(a), 5(b), and 5(c)), the brightness/darkness of the reflected image of the suspected substance 20 (∝ intensity of the regular reflection light L2) is changed only by the change in the line width D of the line portion (dose defect) illustrated in FIGS. 5(a), 5(b), and 5(c).

However, this is effective when the line width D of the line portion of the repetitive pattern 22 (55 nm, for instance) is shorter than the used wavelength (436 nm, for instance). In this case, the aforementioned regular reflection light L2 is generated by an interference of light at the line portion (resist) of the repetitive pattern 22. When the line width D of the line portion of the repetitive pattern 22 changes due to the change in the dose amount at the time of the exposure, the amount of line portion per unit area (namely, the amount of portion at which the aforementioned interference of light is generated) changes and a reflectivity at the line portion changes, thereby the intensity of the regular reflection light L2 may change.

Therefore, after taking the reflected image of the suspected substance 20, the image processor 15 compares brightness information on the reflected image with, for example, brightness information on a reflected image of a desirable sample. The desirable sample is a sample in which a dose amount at a time of an exposure is maintained at a proper value and repetitive patterns 22 with ideal forms (FIG. 5(a)), for instance, are formed on its whole surface.

By setting the brightness value of the reflected image of the desirable sample as a reference, the image processor 15 measures a variation amount of the brightness value of the reflected image of the suspected substance 20. The obtained variation amount of the brightness value represents a variation in the intensity of the regular reflection light L2 caused by the change in the line width D of the line portion of the repetitive pattern 22 (FIGS. 5(a), 5(b), and 5(c)).

Subsequently, the image processor 15 detects the dose defect of the repetitive patterns 22 based on the variation amount of the brightness value in the reflected image of the suspected substance 20 (namely, variation in the intensity of the regular reflection light L2). For instance, if the variation amount of the brightness value is greater than a predetermined threshold value (tolerance value), it may be judged that there is a "defect", on the other hand, if the variation amount is less than the threshold value, the repetitive patterns may be judged to be "normal". Further, it is possible to compare the variation amount of the brightness value in the reflected image of the suspected substance 20 with a predetermined threshold value, instead of using the desirable sample.

As described above, in the second detection method, the repetitive patterns 22 are illuminated by the unpolarized illumination light L1, the reflected image of the suspected substance 20 is taken in accordance with the intensity of the regular reflection light L2 generated from the repetitive patterns 22, and based on the brightness/darkness of the reflected image, the variation in the intensity of the regular reflection light L2 caused by the change in the line width D of the line portion of the repetitive pattern 22 (FIGS. 5(a), 5(b), and 5(c)) is measured.

Therefore, according to the second detection method, although the sufficient detection sensitivity to the defocus defect (FIGS. 4(a), 4(b), and 4(c)) cannot be obtained, it is possible to secure the sufficient detection sensitivity to the dose defect (FIGS. 5(a), 5(b), and 5(c)) of the repetitive patterns 22, so that the dose defect can be selectively detected.

When the detection of defocus defect (FIGS. 4(a), 4(b), and 4(c)) by the first detection method and the detection of dose defect (FIGS. 5(a), 5(b), and 5(c)) by the second detection method are completed in the above-described manner, the surface inspection apparatus 10 of this embodiment detects a final defect of the repetitive patterns 22 based on the two detection results.

For example, a spot on the surface of the suspected substance 20 where at least either of the defocus defect (FIGS. 4(a), 4(b), and 4(c)) or the dose defect (FIGS. 5(a), 5(b), and 5(c)) is detected as a final defect of the repetitive patterns 22. Namely, a logical sum of the result from the first detection method and the result from the second detection method is determined, which is then designated as a final detection result.

As described above, the surface inspection apparatus 10 of this embodiment measures the variation in the intensity or the polarized state of the regular reflection light L2 caused by the change in the shapes of the repetitive patterns 22 (FIGS. 4(a), 4(b), and 4(c), and FIGS. 5(a), 5(b), and 5(c)), and detects the final defect of the repetitive patterns 22 based on both of the measurement results. Accordingly, it is possible to secure the sufficient detection sensitivity to the plurality of types of defects (defocus defect and dose defect) of the repetitive patterns 22.

Further, it is also possible to determine the cause of the defect depending on which of the two detection methods is used to detect the defect. Accordingly, it is also possible to output information on the final defect of the repetitive patterns 22 by adding information on the type of the defect thereto. There are three types of the final defects, which are, a defect detected only by the first detection method (defocus), a defect detected only by the second detection method (dose), and a defect detected by both the first detection method and the second detection method (defocus/dose).

Since the surface inspection apparatus 10 of this embodiment can separately detect the plurality of types of defects of the repetitive patterns 22, it is effective to output the information on the final defect together with the information on the type of the defect and feedback it to an exposure apparatus. By performing such a feedback, an adjustment of the exposure apparatus can be conducted in real time.

Further, it is preferable that in the surface inspection apparatus 10 of this embodiment, the information on the final defect of the repetitive patterns 22 (position on the surface of the suspected substance 20) can be display-output on one image. At this time, it is preferable to change a color and a shape of a mark, for example, for each type of the defects so that the defects can be easily distinguished.

Modified Example

Note that in the aforementioned embodiment, the two polarization plates 34 and 37 are disposed in the cross-Nicole state when detecting the defocus defect using the first detection method, but, the present embodiment is not limited to this. It is allowable that the respective transmission axes of the polarization plates 34 and 37 are set so that they intersect with an angle other than the vertical angle. Specifically, if the respective transmission axes of the polarization plates 34 and 37 intersect, it is possible to execute the detection of the defocus defect using the first detection method. However, the detection sensitivity to the defocus defect becomes the highest when the polarization plates 34 and 37 are disposed in the cross-Nicole state.

Further, in the aforementioned embodiment, the transmission axis of the polarization plate 34 of the illuminating system 13 is disposed in parallel with the plane of incidence 3A of the illumination light L1 (namely, the illumination light L1 is made to be the p-polarized light) when detecting the defocus defect using the first detection method, but, the present embodiment is not limited to this. It is possible to dispose the transmission axis of the polarization plate 34 of the illuminating system 13 orthogonal to the plane of incidence 3A of the illumination light L1 to thereby make the illumination light L1 be s-polarized light. It is also allowable that the transmission axis of the polarization plate 34 is set so that it diagonally crosses the plane of incidence 3A.

Further, in the aforementioned embodiment, the transmission axis of the polarization plate 37 of the light receiving system 14 is disposed orthogonal to the plane of incidence 3A of the illumination light L1 when detecting the defocus defect using the first detection method, but, the present embodiment is not limited to this. It is allowable to dispose the transmission axis of the polarization plate 37 of the light receiving system 14 in parallel with the plane of incidence 3A of the illumination light L1. The transmission axis of the polarization plate 37 may be set so as to diagonally cross the plane of incidence 3A.

Further, in the aforementioned embodiment, the two polarization plates 34 and 37 are retracted from the light paths when detecting the dose defect using the second detection method, but, the present embodiment is not limited to this. Even when either of the polarization plates 34 or 37 is disposed in the light path, the dose defect can be detected based on the variation in the intensity of the regular reflection light L2 from the repetitive patterns 22.

In this case, it is preferable to dispose the polarization plate being either of the polarization plates 34 or 37 whose transmission axis is orthogonal to the plane of incidence 3A of the illumination light L1 (polarization plate 37, in an example in FIG. 1). By disposing the polarization plate in the above-described manner, noise light from a foundation layer of the suspected substance 20 can be reduced, which enables to further enhance the detection sensitivity to the dose defect.

Further, when detecting the dose defect using the second detection method, the respective transmission axes of the polarization plates 34 and 37 may be aligned in parallel while the two polarization plates 34 and 37 are disposed in the light paths. When shifting the detection method from the first detection method to the second detection method, it is only required to rotate at least either of the polarization plates 34 or 37 around an optical axis as a center. In this case, the insertion/removal mechanism (drive motors 4A and 7A) of the polarization plates 34 and 37 become unnecessary.

Further, in the aforementioned embodiment, the detection method is shifted from the first detection method to the second detection method, but, it may be shifted from the second detection method to the first detection method.

Further, in the aforementioned embodiment, a two-dimensional sensor such as a CCD is used as the image sensor 39, but, a one-dimensional sensor can also be applied. In this case, the one-dimensional sensor being an image sensor and a stage on which a semiconductor wafer (or liquid crystal substrate) being a suspected substance is placed are moved in a relative manner, and an image of a whole surface of the semiconductor wafer (or liquid crystal substrate) is taken in such a way that the one-dimensional sensor scans the whole surface of the semiconductor wafer (or liquid crystal substrate).

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A surface state detecting apparatus, comprising:
    a lighting section configured to illuminate a semiconductor pattern formed on a surface of a plate with parallel light;
    a first detecting section configured to detect an intensity caused by a change in shape of the semiconductor pattern based on an intensity of regular reflection light generated from the semiconductor pattern illuminated by the lighting section;
    a second detecting section configured to detect a polarized state of regular reflection light generated from the semiconductor pattern illuminated with polarized light;
    a controller configured to select one of the first detecting section and the second detecting section for surface state detection; and
    a surface state detecting section configured to detect a change in the semiconductor pattern based on a variation in the intensity detected by the first detecting section or a variation in the polarized state detected by the second detecting section.

2. The surface state detecting apparatus according to claim 1, further comprising:
    an output section configured to output a detected information of the surface state detecting section as a signal being able to feed back to a semiconductor manufacturing device which forms the semiconductor pattern.

3. The surface state detecting apparatus according to claim 1, wherein
    the lighting section includes a first polarization plate capable of being inserted into or removed from a light path of the parallel light; and
    the second detecting section includes a second polarization plate capable of being inserted into or removed from a light path of the regular reflection light.

4. The surface state detecting apparatus according to claim 3, wherein
    a transmission axis of the first polarization plate and a transmission axis of the second polarization plate have an intersectional relationship.

5. The surface state detecting apparatus according to claim 1, further comprising:
   a defect detecting section configured to detect a defect of the semiconductor pattern based on a detected information of the surface state detecting section.

6. The surface state detecting apparatus according to claim 1, wherein
   the semiconductor pattern is formed by an exposure; and
   the surface state detecting section is able to detect at least one of a pattern change according to an amount of exposure at a time of the exposure and a pattern change according to a focus condition at the time of the exposure.

7. The surface state detecting apparatus according to claim 1, wherein
   the lighting section configured to collectively illuminate the semiconductor pattern over a length of at least one chip region or more; and
   the surface state detecting section configured to collectively detect a change in the semiconductor pattern which is at least one chip region or more long.

8. A surface state detecting method, comprising:
   illuminating a pattern formed on a surface of an object with parallel light;
   selecting one of a first detection and a second detection, in which the first detection detects an intensity caused by a change in shape of the pattern based on an intensity of regular reflection light generated from the pattern, and the second detection detects a polarized state of regular reflection light generated from the pattern illuminated with polarized light; and
   detecting a surface state using one of the first detection and the second detection.

9. The surface state detecting method according to claim 8, comprising:
   feeding back information of the surface state being detected to a semiconductor manufacturing device which forms the pattern on the surface of the object.

10. The surface state detecting method according to claim 8, comprising:
    disposing a first polarization plate capable of being inserted into or removed from a light path of the parallel light illuminating the object; and
    disposing a second polarization plate capable of being inserted into or removed from a light path of the parallel light reflected from the object.

11. The surface state detecting method according to claim 10, comprising:
    retracting at least one of the first polarization plate and the second polarization plate from the light path during the first detection.

12. The surface state detecting method according to claim 10, comprising:
    disposing the first polarization plate and the second polarization plate in the light path during the second detection.

13. The surface state detecting method according to claim 8, comprising:
    detecting a defect of the pattern based on the surface state being detected.

14. The surface state detecting method according to claim 8, comprising:
    the pattern on the surface of the object is formed by a semiconductor manufacturing device; and
    the method comprises:
      detecting one of a pattern change according to an amount of exposure at a time of the exposure by the semiconductor manufacturing device and a pattern change according to a focus condition at the time of the exposure, based on the surface state being detected.

15. The surface state detecting method according to claim 8, comprising:
    illuminating the object over a region of at least one chip region or more; and
    collectively detecting a change in the region being illuminated.

* * * * *